United States Patent [19]
Lacore et al.

[11] Patent Number: 5,617,589
[45] Date of Patent: Apr. 8, 1997

[54] COMBINATION HEADBAND, EARCOVERS, AND GOGGLES

[76] Inventors: Ernest H. Lacore, 397 Main St., Cromwell, Conn. 06416; Thomas S. Weaver, 32 Locust Hill, Shelburne, Vt. 05482

[21] Appl. No.: 375,294

[22] Filed: Jan. 20, 1995

[51] Int. Cl.⁶ ............................. A61F 9/04; A41D 21/00
[52] U.S. Cl. ........................................ 2/452; 2/209; 2/909
[58] Field of Search ............................. 2/452, 439, 440, 2/436, 426, 209, 909, 918

[56] References Cited

U.S. PATENT DOCUMENTS

| | | | |
|---|---|---|---|
| 4,556,995 | 12/1985 | Yamamoto | 2/452 |
| 4,712,254 | 12/1987 | Daigle | 2/452 |
| 5,309,577 | 5/1994 | Buononato et al. | 2/452 |
| 5,421,037 | 6/1995 | Schulze | 2/452 |

Primary Examiner—Peter Nerbun
Attorney, Agent, or Firm—Donald W. Meeker

[57] ABSTRACT

Winter sports goggles are secured by a two-sided headband made of a double layer of insulating fabric. Downward extensions of the fabric on the sides provide earcovers. The two sides of the headband overlap around the head and are adjustably connected by mating strips of hook and loop fasteners. An advertising logo may be affixed to one or both sides of the headband. The goggles are contoured with a foam edge contacting the face. Foam covered openings on the top and bottom edges of the goggles allow moisture to escape from behind the transparent windscreen which filters ultraviolet rays. A narrow band of elasticized material sewn between the fabric layers of the headband connect each end of the headband to the goggles through a slotted extension from the goggles on each side or through slotted hooks snapping into openings in the sides of the goggles.

8 Claims, 1 Drawing Sheet

COMBINATION HEADBAND, EARCOVERS, AND GOGGLES

BACKGROUND OF THE INVENTION

1. Technical Field

The present invention relates to sports goggles and in particular to a novel combination of winter sports goggles with an adjustable headband and earcovers.

2. Description of the Prior Art

In winter sports such as skiing, snowboarding, snowmobiling, bobsledding, and other high-speed outdoor events, it is necessary to shield the eyes of the athlete from wind, precipitation such as snow, sleet or rain, and the glare of the sun. Additionally, due to the cold temperature and the added wind chill effect of speed, it is necessary to protect the ears of the athlete from the cold to prevent discomfort and avoid frostbite. Athletes also tend to wear headbands to collect perspiration created by the strenuous activity. In cold weather a headband further serves to protect a portion of the head from the cold, and in particular, to protect the temples of the athlete.

Winter sports goggles have developed to a high degree of technical effectiveness in shielding the eyes from wind and ultraviolet rays with an enclosed frame fitting snugly around the contours of the wearer's nose and face with foam padding around the edges of the goggles, while at the same time providing foam covered openings in the edges of the frame to allow moisture to escape and help prevent the goggles from fogging.

However, prior art goggles are generally attached to the head by an elasticized strap around the head of the wearer tension fitting the goggles to the head by drawing the foam frame edges of the goggles snugly against the skin of the wearer to prevent strong airflow on the eyes of the wearer. The prior art goggles with elasticized straps must be pulled on and off over the head of the wearer interferring with glasses, headbands, hats or other headgear. Once the goggles are in place on the head of the wearer, there may be difficulty in finding a proper adjustment to fit an elasticized strap snugly around the head to secure the goggles during vigorous physical activity, while still allowing proper blood circulation and comfort. Often the elasticized straps are relatively narrow and may tend to concentrate the tension to a narrow band around the head, thereby increasing the possibility of interferring with the blood circulation of the wearer. In addition the constant tensioning of the entire elasticized strap in time causes the strap to lose its elasticity and become ineffective.

Headbands which are formed of elasticized material in a closed loop present the same adjustability and comfort problems as the elasticized strap on the prior art goggles. Unless the elasticized headband is exactly the right size for the wearer's head it may be either too tight cutting circulation or too loose slipping out of position. There is an additional measure of discomfort caused by elaticized headbands which are worn over the ears because peoples' ears are especially sensitive to too much tension. The elasticized headbands are also subject to loosing their elasticity over time.

To protect the ears of the winter outdoor athlete, hats pulled down over the ears are often inneffective because the ears are sometimes only partially covered by the hat, as the hat tends to pull upwards. In addition, knit hats generally have a loose knit fabric which is somewhat stretchable and air blows through the knit fabric to chill the ears. Earmuffs are usually quite bulky and the metal band fitting over the top of the head of the wearer presents another element to contend with around the head of the wearer fitting over or under the elasticized strap of the goggles and over or under a hat and or headband, if worn.

Outdoor winter sports have an element of costuming to protect the athlete as well as costuming as a fashion statement. Elasticized straps on goggles are often ugly and often black in color. Earmuffs with their puffy ear protectors and metal over-the-head band are generally not considered to be fashionable.

DISCLOSURE OF INVENTION

The present invention solves the problem of adjustably and comfortably fitting winter sports goggles to the head of the wearer while protecting the ears of the wearer and providing a wide headband which protects against the cold while creating an attractive colorful appearance. One piece of equipment replaces three pieces of equipment normally required to protect the winter athlete adequately (goggles with an elasticized strap, a headband, and ear protectors).

Providing a headband in two pieces connected by hook and loop fasteners, such as the fasteners sold under the trademark VELCRO, with each headband piece attached to one side of the goggles allows the goggles to be secured to and removed from the head of the wearer quickly and easily without interfering with glasses or other head gear.

Using long and wide strips of mating hook and loop fasteners sewn into the fabric of a wide two-piece headband allows the headband to be secured snugly yet comfortably around the head of the wearer at any desired tension adjusted easily by the wearer. The broad width of the band distributes the tension of the band over a far more extensive area of the head to help avoid problems with blood circulation. Attaching each of the two pieces of the headband to the sides of the goggles with a short wide strip of elasticized material in combination with the adjustable mating hook and loop closure fasteners gives the headband just a slight amount of flexing ablity around the head of the wearer useful for movement of the goggles for minor adjustments in the position of the goggles after the main adjustment fit of the hook and loop fasteners has been set. Should the short wide strip of elasticized material lose its elasticity over time, the shortness of the strip versus the adjustable flexibility of the long strip of mating hook and loop fasteners will not cause an appreaciable loss in comfortable and easy adjustment of the headband.

Attaching the two-piece headband with hook and loop fasteners allows the headband to be fabricated from inulated material to provide protection against the cold. The material can also be absorbent to soak up moisture and attractively colored and decorated with stitched, printed, or attached designs or logos.

Providing a wide headband with material extending lower than the goggles creates a portion of the headband on each side of the wearer's head which completely covers each ear of the wearer for comfort and to protect against frostbite. The hook and loop fasteners allow the wearer to adjust the headband to a position which completely covers the wearer's ears while snugly and comfortably fitting the goggles to the face of the wearer.

BRIEF DESCRIPTION OF THE DRAWINGS

These and other details and advantages of our invention will be described in connection with the accompanying drawings, which are furnished only by way of illustration and not in limitation of the invention, and in which drawings.

BEST MODE FOR CARRYING OUT THE INVENTION

Figure 1:
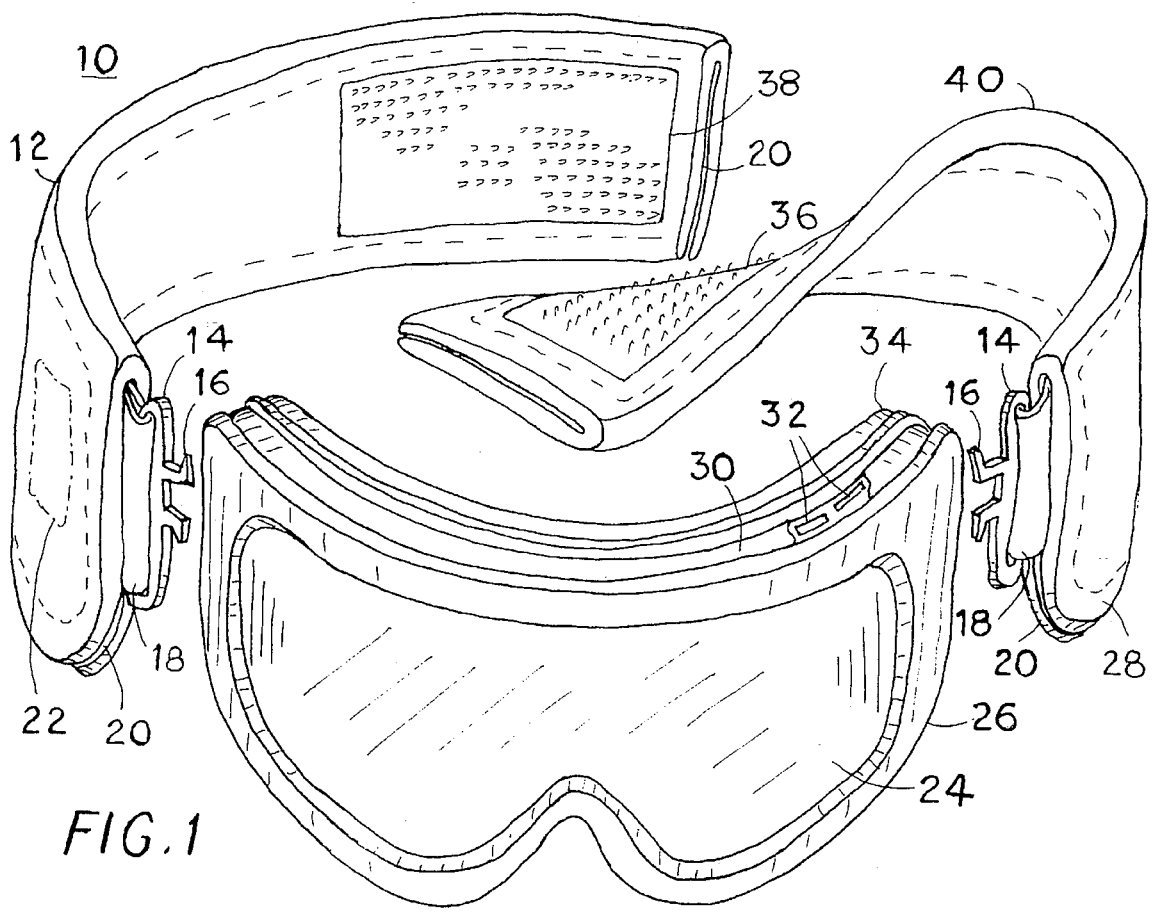
FIG. 1 is a perspective view of the invention with the two headband strips aligned to be attached to the goggles.
Figure 2:
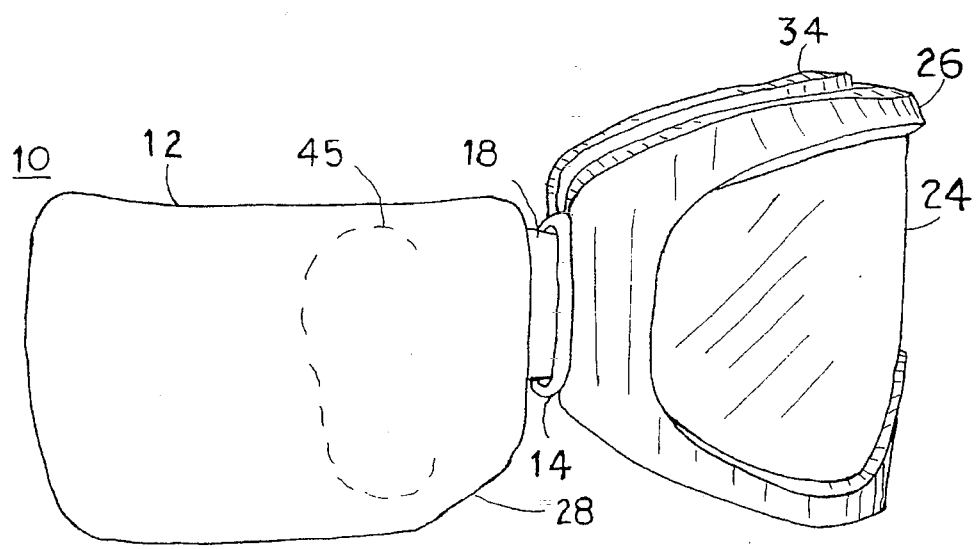
FIG. 2 is a side elevational view of the combination headband, earcovers, and goggles.

In FIGS. 1 and 2 the combination headband, earcovers and goggles 10 comprises outdoor winter sports goggles 26 shaped to fit the contours of a face of a wearer and, attached to each of two side edges of the goggles, a strip of temperature insulating fabric 12 and 40 at least as wide as the side edge of the goggles and sufficiently long to extend around a head of a wearer with a substantial portion of each strip of temperature insulating fabric overlapping each other, and, attached to each of the strips of temperature insulationg fabric, where the the wide strips overlap, mating adjustable connectors 36 and 38 to connect the two strips of temperature insulating fabric. The preferred mating adjustable connectors comprise mating strips of hook and loop fasteners 36 and 38 generally sold under the trademark VELCRO.

Extending downwardly from each of the strips of temperature insulating fabric 12 and 40 a wider (than the side edges of the goggles, as seen in FIG. 2) earcovering portion 28 of the fabric creating an overall width of each of the strips of temperature insulating fabric sufficiently wide to cover an ear 45 (shown dashed in FIG. 2) of a wearer.

Together the goggles 26, overlapping strips of temperature insulating fabric 12 and 40, and the earcovering portion 28 of the fabric create a combination headband, earcovering, and goggles which is attachable around a head of a wearer by abjustably connecting the strips of temperature insulating fabric in an overlapping fashion. An advertising logo 22 may be affixed to at least one strip of temperature insulating material by printing or stitching or attaching a patch by gluing or stitching or other means.

Figure 3:
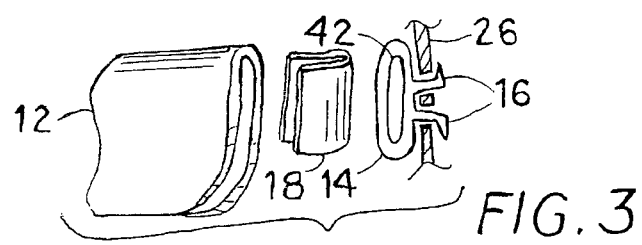
FIG. 3 is a partial perspective view partially in section at a reduced scale showing the components of the headband attaching components.

In FIG. 3 the means of connecting each strip of temperature insulating material to each side of the goggles comprises a strip of elasticized material 18 threaded through a clip slot 42 in an attaching clip 14. A pair of flexible hooks 16 extending from the attaching clip are inserted in two openings in the side edge of the goggles 26, wherein the two openings on each side edge of the goggles are sufficiently large to receive the flexible hooks 16 and the hooks snap into the openings to lock the headband to the goggles. Each strip of elasticized material 18 is inserted in the end of the crease 20 formed by folding over the temperature insulating fabric and the elasticized material is sewn to one end of the strip of temperature insulating fabric. An alternate means of connecting each strip of temperature insulating material would provide an extension of the goggle frame to form a portion of the frame with a frame slot similar to the attaching clip 14 molded to the frame without the flexible hooks, as it appears in FIG. 2. The elasticized strip would be threaded through that slot and attached to the temperature insulating material as above.

The goggles 26 have a strip of foam 34 around an interior edge of the goggles so that the strip of foam is placed to engage a face of a wearer for a snug comfortable fit. The goggles 26 further comprise at least one transparent screen 24 for shielding wind and filtering ultraviolet rays. Ventilation openings 32 along a top edge and a bottom edge of the goggles allow moisture to escape while a thin foam covering 30 over the holes prevents wind from entering the goggles through the ventilation openings.

The goggles are preferrably fabricated of molded plastic and the headband is preferrably fabricated of a doubled over sheet of fleece or other soft warm material with insulating properties and absorption properties.

The headband, earcovering goggles are easily attached to a head of a wearer by pulling back the two ends of the headband while positioning the goggles in place and positioning the earcovering portion over the ears, and then connecting the hook and loop fasteners for a comfortable tension around the head of the wearer. Minor adjustments of the goggles may be made with the hook and loop fasteners connected because of the short elastic strips connecting the headband strips to the goggles.

It is understood that the preceding description is given merely by way of illustration and not in limitation of the invention and that various modifications may be made thereto without departing from the spirit of the invention as claimed.

We claim:

1. A combination headband, earcovers and goggles comprising:

outdoor winter sports goggles shaped to fit the contours of a face of a wearer, wherein the outdoor winter sports goggles have two side edges;

attached to each of the two side edges of the goggles a strip of soft absorbent temperature insulating fabric at least as wide as the side edge of the goggles and sufficiently long to extend around a head of a wearer with a substantial portion of each strip of temperature insulating fabric overlapping each other, the temperature insulating fabric fabricated to soak up moisture and provide protection against the cold;

attached to each of the wide strips of temperature insulating fabric, where the wide strips overlap, mating adjustable connectors to connect the two strips of temperature insulating fabric with an adjustable connection for a comfortable fit;

an earcovering portion, wider than the side edges of the goggle, on the temperature insulating fabric, said earcovering portion having a width sufficiently wide to cover an ear of the wearer so that the soft absorbent temperature insulating fabric contacts the ear with an adjustable fit as the wide strips are connected;

wherein the temperature insulating fabric is folded over double along each strip;

connecting means for connecting each strip of temperature insulating fabric to each side of the goggles, a strip of elasticized material sewn between the folded over temperature insulating fabric, said strip of elasticized material being attached to said connecting means, so that minor adjustments of the goggles are possible after the wide strips are connected;

wherein the goggles, overlapping strips of temperature insulating fabric, and the earcovering portion of the fabric create a combination headband, earcovering, and goggles which is attachable around a head of a wearer by adjustably connecting the strips of temperature insulating fabric in an overlapping fashion.

2. The invention of claim 1 wherein the mating adjustable connectors comprise mating strips of hook and loop fasteners.

3. The invention of claim 2 further comprising, between each strip of elasticized material and each side of the goggles, an attaching clip having a clip slot to receive the strip of elasticized material threaded through the clip slot and the attaching clip having a pair of flexible hooks extending from the attaching clip, wherein each side of the goggles further comprises two openings sufficiently large to receive the flexible hooks and the hooks snap into the openings to lock the headband to the goggles, and wherein each strip of elasticized material is sewn to one of the strips of temperature insulating fabric.

4. The invention of claim 2 further comprising, between each strip of elasticized material and each side of the goggles an extension of the goggles forming a frame slot to receive the strip of elasticized material threaded through the frame slot and wherein each strip of elasticized material is sewn to one of the strips of temperature insulating fabric.

5. The invention of claim 3 further comprising affixing an advertising logo to at least one strip of temperature insulating fabric.

6. The invention of claim 5 wherein the goggles further comprise a strip of foam around an interior edge of the goggles so that the strip of foam is placed to engage a face of a wearer.

7. The invention of claim 6 wherein the goggles further comprise at least one transparent screen for shielding wind and filtering ultraviolet rays.

8. The invention of claim 7 wherein the goggles further comprise ventilation openings along a top edge and a bottom edge of the goggles for moisture to escape and a layer of foam covering the ventilation openings.

* * * * *